United States Patent [19]

Roos et al.

[11] Patent Number: 5,783,576
[45] Date of Patent: Jul. 21, 1998

[54] BENZOYL GUANIDINE DERIVATIVES, THE PREPARATION THEREOF AND THEIR USE IN PHARMACEUTICAL COMPOSITIONS

[75] Inventors: Otto Roos, Schwabenheim; Georg Speck, Ingelheim; Walter Losel, Gau-Algesheim; Dietrich Arndts; Wolf-Dietrich Bechtel, both of Appenheim, all of Germany

[73] Assignee: Boehringer Ingelheim KG, Ingelheim am Rhein, Germany

[21] Appl. No.: 649,614

[22] PCT Filed: Oct. 31, 1994

[86] PCT No.: PCT/EP94/03581

§ 371 Date: Aug. 9, 1996

§ 102(e) Date: Aug. 9, 1996

[87] PCT Pub. No.: WO95/12584

PCT Pub. Date: May 11, 1995

[30] Foreign Application Priority Data

Nov. 4, 1993 [DE] Germany ............ 43 37 611.8

[51] Int. Cl.$^6$ .......... C07D 401/04; C07D 247/02; A61K 31/495; A61K 31/505
[52] U.S. Cl. .......... 514/242; 514/243; 514/248; 514/249; 514/252; 514/253; 514/256; 514/259; 514/267; 514/272; 514/273; 514/274; 514/307; 514/309; 514/310; 514/311; 514/312; 514/313; 514/314; 514/316; 514/317; 514/318; 514/326; 514/329; 514/331; 514/332; 514/401; 514/403; 514/426; 514/429; 514/618; 514/619; 514/620; 544/182; 544/183; 544/224; 544/235; 544/237; 544/250; 544/284; 544/287; 544/293; 544/295; 544/296; 544/291; 544/292; 544/309; 544/310; 544/311; 544/312; 544/315; 544/316; 544/317; 544/319; 544/321; 544/322; 544/323; 544/324; 544/325; 544/328; 544/329; 544/331; 544/332; 544/333; 544/335; 544/336; 544/346; 544/350; 544/353; 544/357; 544/360; 544/363; 544/392; 544/400; 544/405; 544/406; 544/407; 544/408; 544/409; 546/119; 546/141; 546/143; 546/145; 546/146; 546/187; 546/188; 546/191; 546/192; 546/194; 546/199; 546/200; 546/208; 546/216; 546/221; 546/224; 546/231; 546/273.4; 546/274.1; 546/275.4; 546/276.4; 546/279.1; 548/300.1; 548/302.7; 548/379.1; 548/557; 548/559; 548/567; 564/162; 564/164; 564/167; 564/168

[58] Field of Search .......... 546/119, 141, 546/143, 145, 146, 187–8, 191, 192, 194, 199, 208, 216, 221, 224, 231, 273.4, 274.1, 275.4, 276.4, 279.1; 544/182, 183, 224, 235, 237, 250, 284, 287, 293, 295, 296, 291–2, 309–312, 315–17, 319, 321–5, 328, 329, 331–3, 335, 336, 346, 350, 353, 357, 360, 363, 392, 400, 405–409; 548/300.1, 302.7, 379.1, 557, 559, 567; 564/162, 164, 167, 168; 514/242, 243, 248, 249, 252, 253, 255, 256, 259, 267, 272–4, 307, 309, 310–14, 316–8, 332, 326, 329, 331, 401, 403, 426, 429, 618, 619, 620

[56] References Cited

U.S. PATENT DOCUMENTS 3,953,476 4/1976 Cragoe, Jr. ............ 260/347.2

FOREIGN PATENT DOCUMENTS 589336 3/1994 European Pat. Off. .
603650 6/1994 European Pat. Off. .

Primary Examiner—Mark L. Berch
Attorney, Agent, or Firm—R. P. Raymond; M-E. M. Devlin; A. R. Stempel

[57] ABSTRACT

New compounds of general formula (I) are provided:

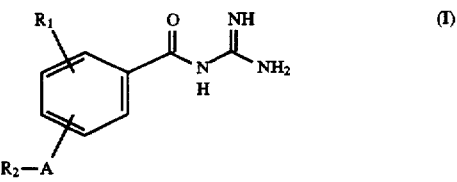

which are explained in the specification can be prepared by a variety of methods. The compounds may be used in pharmaceutical compositions.

4 Claims, No Drawings

BENZOYL GUANIDINE DERIVATIVES, THE PREPARATION THEREOF AND THEIR USE IN PHARMACEUTICAL COMPOSITIONS

The invention relates to new benzoyl guanidine derivatives, processes for the preparation thereof and their use in the manufacture of pharmaceutical compositions.

According to one aspect of the invention, we provide compounds of the formula (I)

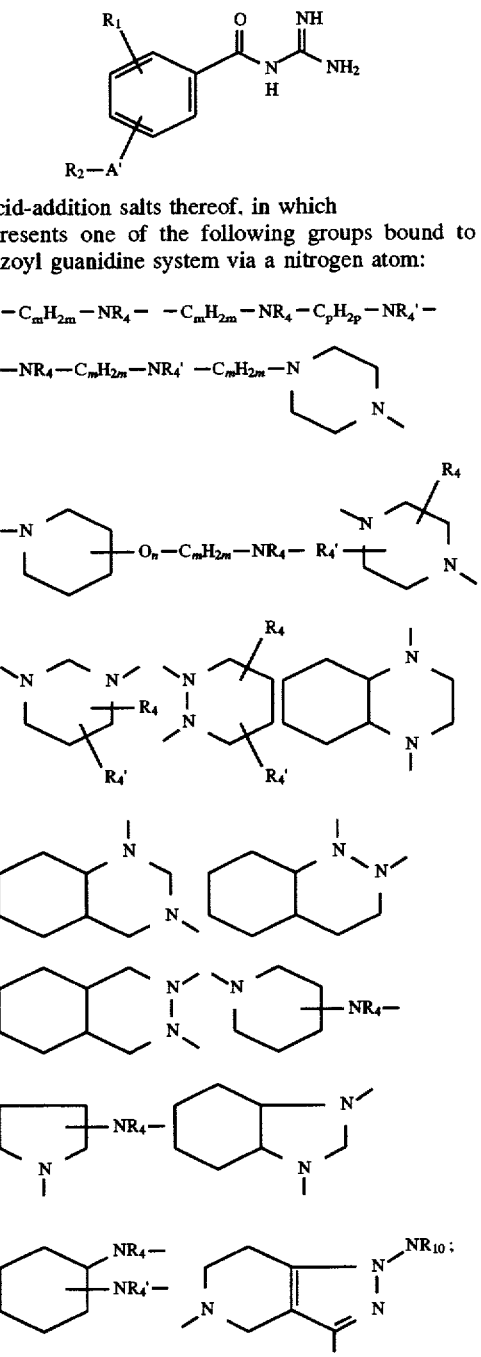

and acid-addition salts thereof, in which

A represents one of the following groups bound to the benzoyl guanidine system via a nitrogen atom:

$R_1$ denotes F, Cl, $CF_3$, R'—$SO_2$— or R'—NH—$SO_2$— (R' being $C_{1-5}$-alkyl, halogen- or phenyl-substituted $C_{1-5}$-alkyl; in which the phenyl groups may contain up to three substituents selected from the group halogen, $C_{1-4}$-alkyl or $C_{1-4}$-alkoxy).

$R_2$ denotes a group of formula

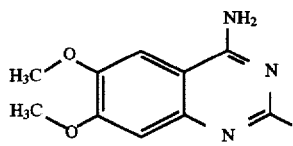 (II)

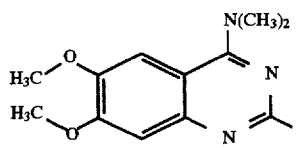 (III)

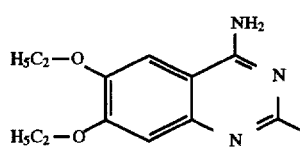 (IV)

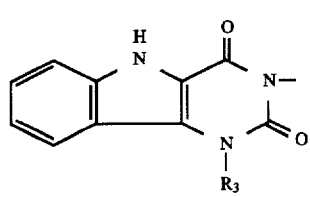 (V)

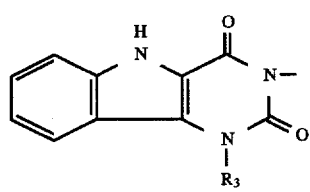 (VI)

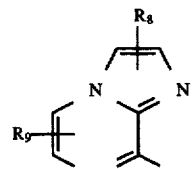 (VII)

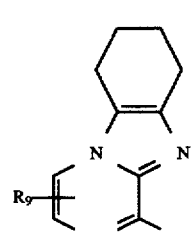 (VIII)

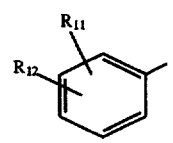 (IX)

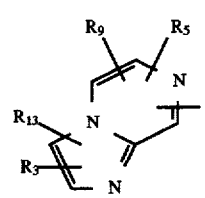 (X)

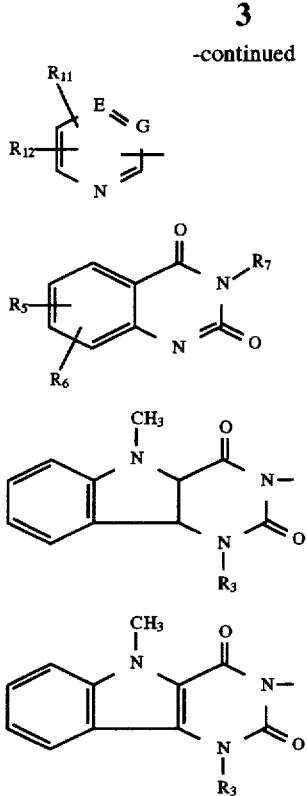

wherein $R_3$, $R_4$ and $R_4'$, which may be the same or different, denote hydrogen, $C_{1-4}$-alkyl, or $R_4$ and $R_4'$ may also denote phenyl, benzyl and $C_{3-7}$-cycloalkyl;

$R_5$ and $R_6$, which may be the same or different, denote hydrogen, methyl, methoxy, hydroxy or halogen;

$R_7$ denotes hydrogen, $C_{1-4}$-alkyl, benzyl or benzyloxy;

$R_8$ and $R_9$, which may be the same or different, denote hydrogen, $C_{1-4}$-alkyl, phenyl or halogen;

$R_{10}$ denotes hydrogen or $C_{1-6}$-alkyl, which may also be substituted by phenyl or methyl-, methoxy- or halogen-substituted phenyl;

$R_{11}$ and $R_{12}$, which may be the same or different, denote hydrogen, methyl, methoxy, phenyl, benzyl, nitro, cyano, halogen, trifluoromethyl, amino, $NR_{10}R_{13}$, 1-pyrrolidinyl, 1-pyrazolinyl, 1-imidazolidihyl, 1-piperidinyl, 1-piperazinyl or carbamoyl and $R_{11}$ can also denote a benzene ring condensed to these systems which may carry up to three substituents selected from the group methyl, methoxy, halogen, $CF_3$ and CN;

$R_{13}$ denotes hydrogen, halogen, $C_{1-4}$-alkyl, which may also be substituted by phenyl, phenoxy or benzyloxy; and E and G, which may be identical or different, denote N or CH, m denotes 2, 3, 4, 5 or 6, n denotes 0 or 1 and p denotes 2, 3 or 4.

The alkyl, alkenyl, alkynyl and alkylene groups mentioned in the above definitions may be straight-chained or branched. Lower groups have 1 to 4, particularly 1 to 3 and more especially 1 or 2 carbon atoms. Of the halogens, fluorine, chlorine and bromine and particularly fluorine and chlorine are preferred. The preferred unsaturated hydrocarbon groups are alkyl and propargyl. The letter m preferably denotes 2, 3 or 4 whilst p preferably denotes 2 or 3.

Where the new compounds may exist in different stereoisomeric or cis/trans-isomeric forms, the above formulae indicate the pure forms and mixtures thereof. The invention includes all stereoisomeric and cis/trans-isomeric forms, whether optically pure or in the form of mixtures thereof.

The groups $R_2$—A— typically have structures of which those shown below are representative:

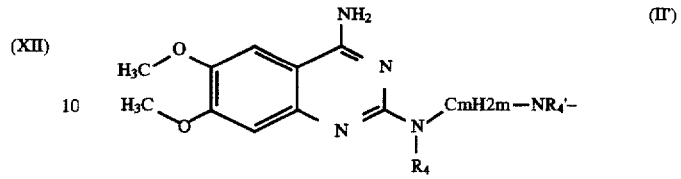

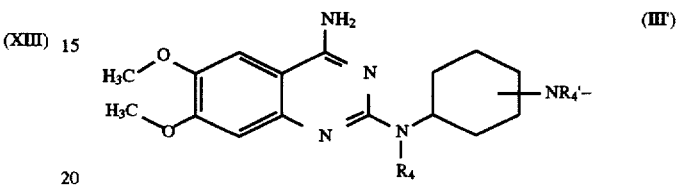

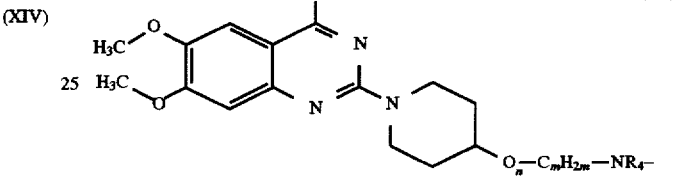

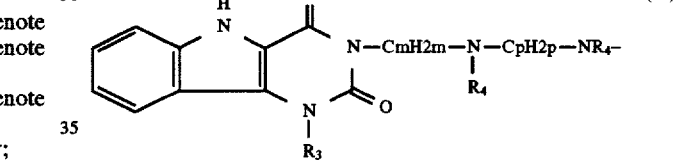

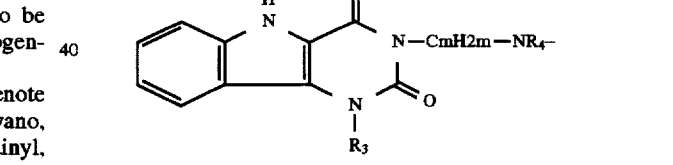

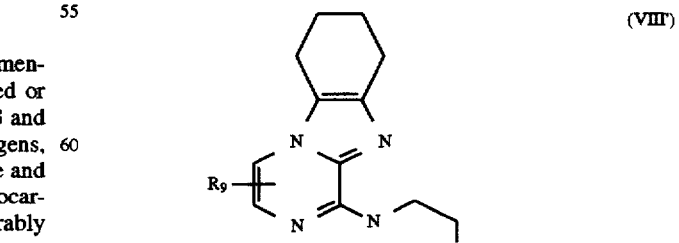

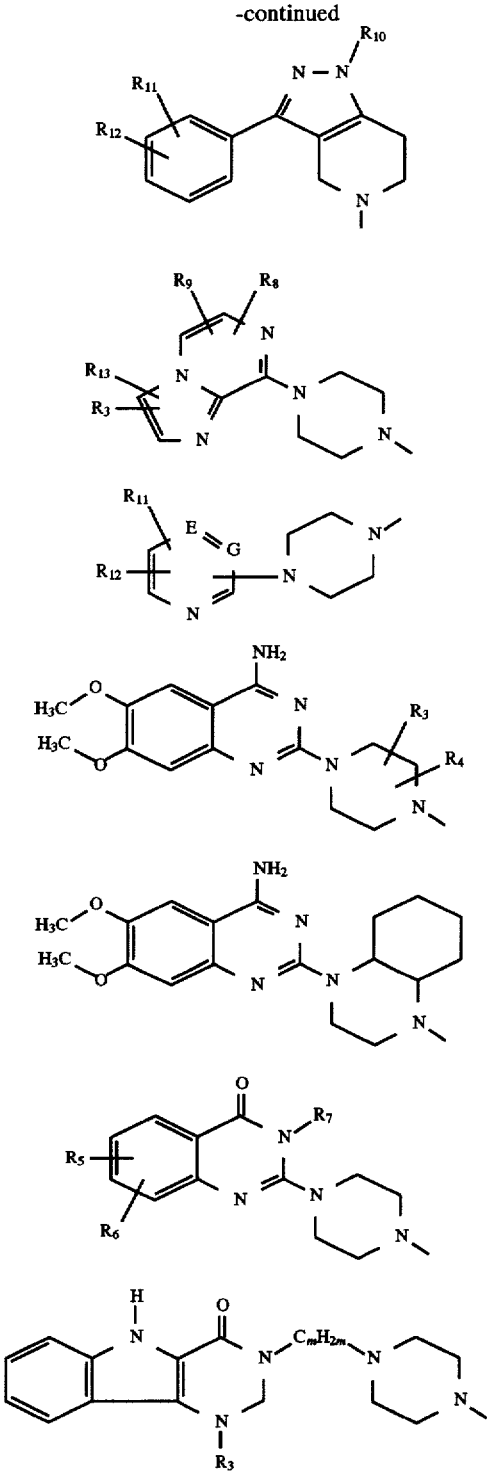

and if A is bound via a nitrogen atom to the group R₂, generally a group A is present in which the bond from R₂ starts from a carbon atom as in (II'), (III') and IV').

The new compounds may be obtained by various methods, which comprise a further feature of the invention. Such methods include various processes known per se. Examples of processes according to the invention are a) reaction of a compound of formula

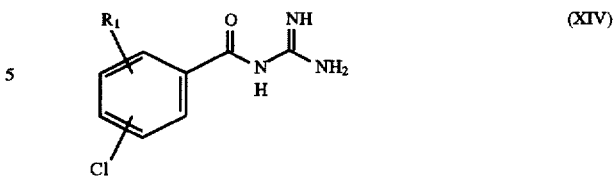

with an amine of formula $$R_2\text{—A—H} \quad (XVII)$$

wherein $R_1$ and $R_2$ are as hereinbefore defined;

b) in order to prepare those compounds of formula (I) wherein $R_1$ represents a group of formula II, III, or IV, the link may also be built up using another nitrogen of the radical $R_2$. For example, compounds in which R2 denotes II can be prepared by reacting an amine of the general formula

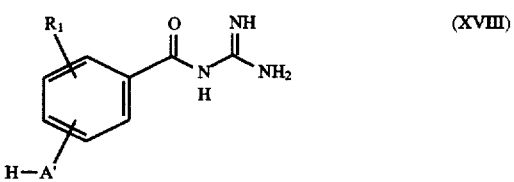

wherein A' is a group A which is bound via a nitrogen to $R_2$ as in II', III' or IV', and $R_1$ is as hereinbefore defined with a chinazolon derivative of general formula

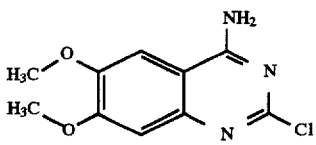

as described in (a) above c) reaction of a compound of formula

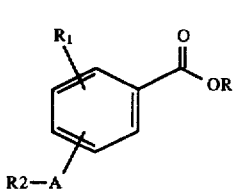

wherein R is a lower alkyl group or benzyl group, and $R_1$, $R_2$ and A are as hereinbefore defined, which guanidine.

In reaction (a) above, the reaction is generally carried out at elevated temperature in a polar solvent or mixture of solvents, anhydrous if possible, particularly dimethylsulphoxide or dimethylformamide, and preferably in the presence of a base such as triethylamine, N-methylpiperidine or pyridine.

In reaction (c) above, the reaction is not restricted to the esters wherein R is as hereinbefore defined, the person skilled in the art will conveniently use an ester which is easy to prepare, such as the methyl- or ethylester, or an ester which produces an alcohol which will not affect the reaction or cause problems when it is formed.

It is preferable to use as a solvent for the reaction the alcohol which is also contained in the ester group, e.g. by reacting a methylester of formula XX in methanol at its boiling point. This method is most suitable for preparing the compounds according to the invention.

Where the compounds of formula (I) can occur in stereoisomeric or other isomeric forms, corresponding starting materials are used. Alternatively, any mixtures which may be formed during production may be separated into their components.

Those starting materials which are not already known can also be obtained by conventional methods. If, for example, instead of the N-amidino-carboxamides of formula XVI or XVIII the corresponding esters are used, the starting materials of formula XX are obtained.

The compounds of formula I can be used as active substances in pharmaceutical compositions or may be used as intermediate products for preparing such active substances. Among other things, the new compounds inhibit $Na^+/H^+$- and $Na^+/Li^+$-exchange. The active substances according to the invention can be used as antihypertensives, mucolytics, diuretics and cancerostatics; they can also be used for treating diseases connected with ischaemia (for example cardiac, cerebral, gastrointestinal, pulmonary and renal ischaemia, ischaemia of the liver, or ischaemia of the skeletal musculature). Corresponding diseases include, for example, coronary heart disease, Angina pectoris, embolism in the circulation of the lungs, acute or chronic kidney failure, chronic kidney insufficiency, cerebral infarction (e.g. after the re-circulation of the blood through areas of the brain after vascular blockages have been opened up, in conjunction with t-PA, streptokinase, urokinase, etc.), acute and chronic blood flow disorders in the brain. In reperfusion of the ischaemic heart (e.g. after an attack of Angina pectoris or cardiac infarction) irreversible damage may be caused to cardiomyocytes in the affected region. The compounds according to the invention may be used in such cases for cardioprotection, inter alia. The new compounds are distinguished by their minimal side effects, the virtual absence of α1- and/or α2-effects being particularly noteworthy.

The field of applications concerning ischaemia also includes the prevention of damage to transplants (e.g. as protection for the transplanted organ, during and after implantation), which may occur in connection with transplantation.

The active substances may be administered in conventional formulations, such as plain or coated tablets, capsules, granules, injectable solutions or, possibly, preparations administered nasally, the quantity of active substance per unit dose generally ranging from 1 to 200 mg, preferably from 20–100 mg. Pharmaceutical compositions comprising a compound of the invention in association with a physiologically acceptable carrier, diluent or excipient comprise a further feature of the invention.

These pharmaceutical forms may be prepared in known manner, and are illustrated by the following non-limiting Examples.

Pharmacy Examples
1. Tablets (composition)

| Compound according to Example | 40.0 mg |
| --- | --- |
| Corn starch | 144.0 mg |
| sec. Calcium phosphate | 115.0 mg |
| Magnesium stearate | 1.0 mg |
| | 300.0 mg |

2. Gelatine capsules

The contents of a capsule consist of 50.0 mg of a compound according to the invention and 150.0 mg of corn starch.

The examples of synthesis which follow illustrate aspects of the invention.

The following Tables list compounds derived from the following formula (Ia):

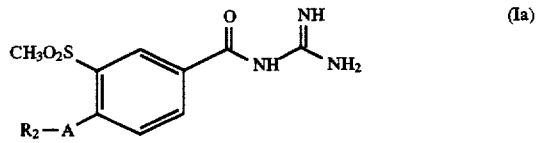

EXAMPLE 1

N-[2-(4-Amino-6,7-dimethoxy)quinazolinyl]-N'-[1-[4-(N-amidino-carbamoyl)-2-methylsulphonyl]phenyl]-N,N'-dimethyl-1,2-diaminoethane-hydrochloride

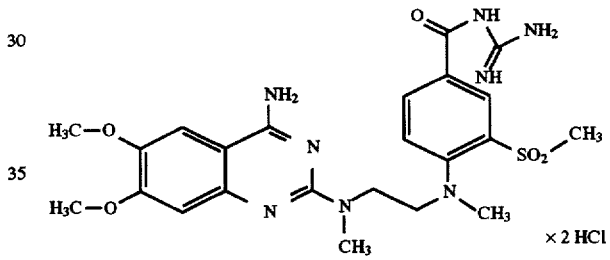

(a) 11.65 g of N-[(4-amino-6,7-dimethoxy)-2-quinazolinyl]-N,N'-dimethyl-1,2-diaminoethane (40 mmol), 99 g of 4-chloro-3-methylsulphonyl-benzoic acid methylester (40 mmol) and 6.1 ml of triethylamine are reacted in 55 ml of dimethylsulphoxide for 2 hours at 80° C. After cooling, 90 ml of water are added and the reaction product precipitates out and is collected by suction filtration and the substance is used for the next step without further purification. Yield: 14.7 g of solid substance.

(b) 14.7 g of the ester obtained according to (a) is suspended in 200 ml of dimethylformamide, reacted with a filtered guanidine solution of 11.9 g of guanidine hydrochloride, 90 ml of methanol and 2.9 g of sodium and stirred for 30 min., while refluxing (100° C. oil bath), during which the methanol is distilled off. The reaction mixture is concentrated to residue and purified over silica gel, using ethyl acetate 70/isopropanol 30/dimethylformamide 10/ammonia 5. The product obtained is dissolved in acetone/dimethylformamide and converted into its dihydrochloride. Yield: 16.2 g, Mp. >250° C.

EXAMPLE 2

N-[2-(4-Amino-6,7-dimethoxy)quinazolinyl]-N'-[1-[4-(N-amidino-carbamoyl)-2-methyl-sulfonyl]phenyl]-N, N'-piperazine-di-hydrochloride

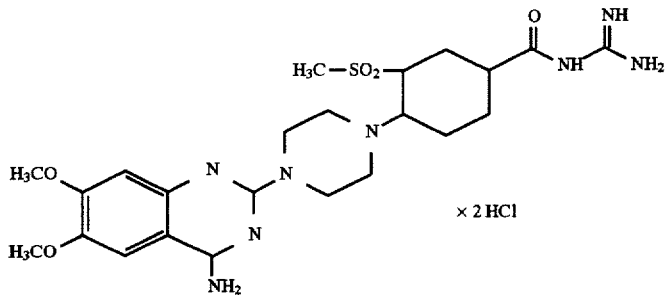

5.8 g (19.44 mmol) 4-piperazinyl-3-methyl-sulfonyl-benzoic acid methylester, 4.65 g (19.44 mmol) 1-amino-3-chloro-6,7-dimethoxy quinazoline and 2.02 g (20 mmol) triethylamine are refluxed in 115 ml n-amyl alcohol for 1.5 h. After cooling to room temperature the product crystallizes and is collected by suction filtration (6.37 g)

2.06 g of the ester obtained according to step (a) are added to a guanidine solution obtained from 1.91 g (20 mmol) guanidine hydrochloride and 20 mmol sodium hydride in 40 ml dimethylformamide. The resulting mixture is heated to 100°–110° C. under nitrogen for 2 h. After cooling to room temperature, insolubles are filtered off and the filtrate is concentrated under vacuum to dryness and the residue is chromatographically purified on a silica gel column using solution of ethyl acetate 70/isopropanol 30/ammonia 5 as eluate. From methanolic hydrochloride solution there were obtained 1.2 g of the title compound having a melting point of Fp. =240°–243° C.

The compounds shown in the following Tables can be obtained in accordance with the above Examples and/or the data in the specification.

TABLE 1

Compounds of formula Ia wherein $R_2$-A- is a group of formula II'

| No. | m | $R_4'$ | $R_4$ | Mp. [°C.] |
|---|---|---|---|---|
| 1 | 2 | H | H | |
| 2 | 2 | $CH_3$ | H | |
| 3 | 2 | H | $CH_3$ | |
| 4 | 2 | $CH_3$ | $CH_3$ | |
| 5 | 2 | $CH_3$ | $C_2H_5$ | |
| 6 | 2 | $C_2H_5$ | $CH_3$ | |
| 7 | 2 | $C_2H_5$ | $C_2H_5$ | |
| 8 | 2 | i-$C_3H_7$ | $CH_3$ | |
| 9 | 2 | $CH_3$ | i-$C_3H_7$ | |
| 10 | 2 | i-$C_3H_7$ | i-$C_3H_7$ | |
| 11 | 3 | H | $CH_3$ | |
| 12 | 3 | $CH_3$ | H | |
| 13 | 3 | $CH_3$ | $CH_3$ | |
| 14 | 3 | $C_2H_5$ | $CH_3$ | |
| 15 | 3 | $CH_3$ | $C_2H_5$ | |
| 16 | 3 | $C_2H_5$ | $C_2H_5$ | |
| 17 | 3 | i-$C_3H_7$ | $CH_3$ | |
| 18 | 3 | $CH_3$ | i-$C_3H_7$ | |
| 19 | 3 | i-$C_3H_7$ | i-$C_3H_7$ | |
| 20 | 3 | n-$C_4H_9$ | n-$C_4H_9$ | |

TABLE 2

Compounds of formula Ia wherein $R_2$-A is a group of formula III'

| No. | $R_4'$ | $R_4$ | Form | Mp. [°C.] |
|---|---|---|---|---|
| 1 | H | H | cis | |
| 2 | $CH_3$ | H | cis | |
| 3 | H | $CH_3$ | cis | |
| 4 | $CH_3$ | $CH_3$ | cis | |
| 5 | n-$C_3H_7$ | n-$C_3H_7$ | cis | |
| 6 | H | H | trans | |
| 7 | $CH_3$ | H | trans | |
| 8 | H | $CH_3$ | trans | |
| 9 | $CH_3$ | $CH_3$ | trans | |
| 10 | n-$C_3H_7$ | n-$C_3H_7$ | trans | |
| 11 | i-$C_4H_9$ | H | cis/trans | |
| 12 | H | t-$C_4H_9$ | cis/trans | |

TABLE 3

Compounds of formula Ia wherein $R_2$-A is a group of formula IV'

| No. | m | n | $R_4$ | Mp. [°C.] |
|---|---|---|---|---|
| 1 | 2 | 0 | H | |
| 2 | 2 | 0 | $CH_3$ | |
| 3 | 2 | 0 | $C_2H_5$ | |
| 4 | 2 | 0 | i-$C_3H_7$ | |
| 5 | 2 | 0 | $C_6H_5$ | |
| 6 | 2 | 1 | H | |
| 7 | 2 | 1 | $CH_3$ | |
| 8 | 2 | 1 | $C_2H_5$ | |
| 9 | 2 | 1 | i-$C_3H_7$ | |
| 10 | 2 | 1 | $C_6H_5$ | |
| 11 | 3 | 0 | H | |
| 12 | 3 | 0 | $CH_3$ | |
| 13 | 3 | 0 | $C_2H_5$ | |
| 14 | 3 | 0 | i-$C_3H_7$ | |
| 15 | 3 | 0 | $C_6H_5$ | |
| 16 | 3 | 1 | H | |
| 17 | 3 | 1 | $CH_3$ | |
| 18 | 3 | 1 | $C_2H_5$ | |
| 19 | 3 | 1 | i-$C_3H_7$ | |
| 20 | 3 | 1 | $C_6H_5$ | |

TABLE 4

Compounds of formula Ia wherein $R_2$-A is a group of formula V', $R_3$ is H and p is 2

| No. | m | $R_4$' | $R_4$ | Mp. [°C.] |
|---|---|---|---|---|
| 1 | 2 | H | H | |
| 2 | 2 | $CH_3$ | $CH_3$ | |
| 3 | 2 | $C_2H_5$ | $C_2H_5$ | |
| 4 | 2 | i-$C_3H_7$ | i-$C_3H_7$ | |
| 5 | 2 | $C_6H_5$ | $CH_3$ | |
| 6 | 3 | H | H | |
| 7 | 3 | $CH_3$ | $CH_3$ | |
| 8 | 3 | $C_2H_5$ | $C_2H_5$ | |
| 9 | 3 | i-$C_3H_7$ | i-$C_3H_7$ | |
| 10 | 3 | $C_6H_5$ | $CH_3$ | |
| 11 | 2 | n-$C_4H_9$ | $CH_3$ | |
| 12 | 2 | $C_6H_5$ | $C_6H_5$ | |

TABLE 5

Compounds of formula Ia wherein $R_2$-A is a group of formula VI

| No. | m | $R_4$ | $R_3$ | Mp. [°C.] |
|---|---|---|---|---|
| 1 | 2 | H | H | |
| 2 | 2 | $CH_3$ | $CH_3$ | |
| 3 | 2 | $C_2H_5$ | $C_2H_5$ | |
| 4 | 2 | i-$C_3H_7$ | i-$C_3H_7$ | |
| 5 | 2 | $C_6H_5$ | $CH_3$ | |
| 6 | 3 | H | H | |
| 7 | 3 | $CH_3$ | $CH_3$ | |
| 8 | 3 | $C_2H_5$ | $C_2H_5$ | |
| 9 | 3 | i-$C_3H_7$ | i-$C_3H_7$ | |
| 10 | 3 | $C_6H_5$ | $CH_3$ | |
| 11 | 2 | n-$C_4H_9$ | $CH_3$ | |
| 12 | 2 | $C_6H_5$ | $C_6H_5$—$CH_2$ | |

TABLE 6

Compounds of formula Ia denotes a group of formula VII

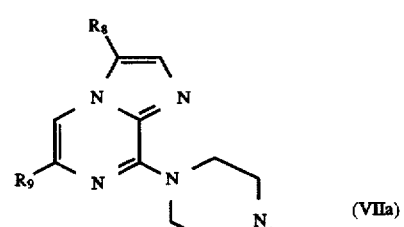

(VIIa)

| No. | $R_8$ | $R_9$ | Mp. [°C.] |
|---|---|---|---|
| 1 | H | H | |
| 2 | $CH_3$ | Cl | |
| 3 | Cl | Cl | |
| 4 | $CH_3$ | $CH_3$ | |

TABLE 7

Compounds of formula Ia wherein $R_2$-A denotes a group of formula VIII

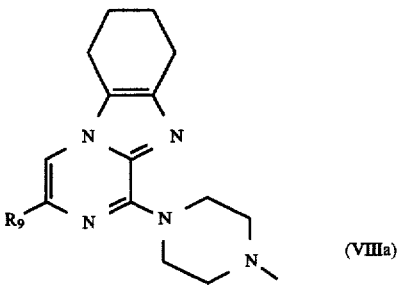

(VIIIa)

| No. | $R_9$ | Mp. [°C.] |
|---|---|---|
| 1 | H | |
| 2 | Cl | |
| 3 | $CH_3$ | |

TABLE 8

Compounds of formula Ia wherein $R_2$-A denotes a group of formula IX (the positional data for $R_{11}/R_{12}$ relate to the phenyl group)

| No. | $R_{10}$ | $R_{11}$ | $R_{12}$ | Mp. [°C.] |
|---|---|---|---|---|
| 1 | H | H | H | |
| 2 | H | 3-Cl | H | |
| 3 | H | 2-F | 3-F | |
| 4 | H | 4-$NO_2$ | H | |
| 5 | H | 4-CN | H | |
| 6 | H | 3-$OCH_3$ | 4-$OCH_3$ | |
| 7 | H | $CH_3$ | H | |
| 8 | H | 4-F | 3-$C_2H_5$ | |
| 9 | H | 4-$CH_2$—$C_6H_5$ | H | |
| 10 | H | 4-$OCH_3$ | 2-$CH_2$—$C_6H_5$ | |
| 11 | $CH_3$ | H | H | |
| 12 | $CH_3$ | 3-Cl | H | |
| 13 | $CH_3$ | 2-F | 3-F | |
| 14 | $CH_3$ | 4-$NO_2$ | H | |
| 15 | $CH_3$ | 4-CN | H | |
| 16 | $CH_3$ | 3-$OCH_3$ | 4-$OCH_3$ | |
| 17 | $CH_3$ | $CH_3$ | H | |
| 18 | $CH_3$ | 4-F | 3-$C_2H_5$ | |
| 19 | $CH_3$ | 4-$CH_2$—$C_6H_5$ | H | |
| 20 | $CH_3$ | 4-$OCH_3$ | 2-$CH_2$—$C_6H_5$ | |
| 21 | $C_2H_5$ | H | H | |
| 22 | $C_2H_5$ | 3-Cl | H | |
| 23 | $C_2H_5$ | 2-F | 3-F | |
| 24 | $C_2H_5$ | 4-$NO_2$ | H | |
| 25 | $C_2H_5$ | 4-CN | H | |
| 26 | $C_2H_5$ | 3-$OCH_3$ | 4-$OCH_3$ | |
| 27 | $C_2H_5$ | $CH_3$ | H | |
| 28 | $C_2H_5$ | 4-F | 3-$C_2H_5$ | |
| 29 | $C_2H_5$ | 4-$CH_2$—$C_6H_5$ | H | |
| 30 | $C_2H_5$ | 4-$OCH_3$ | 2-$CH_2$—$C_6H_5$ | |
| 31 | i-$C_3H_7$ | H | H | |
| 32 | n-$C_6H_{13}$ | 4-F | H | |
| 33 | 4-F-$C_6H_4$ | 4-F | H | |
| 34 | $CH_2$—$C_6H_5$ | 4-F | H | |
| 35 | $C_2H_5$ | 4-F | H | |
| 36 | n-$C_4H_9$ | 2-$CH_3$ | 6-$CH_3$ | |

TABLE 9

Compounds of formula Ia wherein $R_2$-A is a group of formula X':

![Structure Xa] (Xa)

($R_3$ and $R_9$ represent H)

| No. | $R_8$ | $R_{13}$ | Mp. [°C.] |
|---|---|---|---|
| 1 | H | H | |
| 2 | $C_2H_5$ | H | |
| 3 | H | $CH_3$ | |
| 4 | i-$C_3H_7$ | H | |
| 5 | i-$C_3H_7$ | $CH_3$ | |
| 6 | H | Br | |
| 7 | Br | H | |
| 8 | $CH_3$ | H | |

TABLE 9a

Compounds of formula Ia wherein $R_2$-A is a group of formula X'

![Structure Xb] (Xb)

($R_3$ and $R_9$ represent H)

| No. | $R_8$ | $R_{13}$ | Mp. [°C.] |
|---|---|---|---|
| 1 | H | H | |
| 2 | $C_2H_5$ | H | |
| 3 | H | $CH_3$ | |
| 4 | i-$C_3H_7$ | H | |
| 5 | i-$C_3H_7$ | $CH_3$ | |
| 6 | H | Br | |
| 7 | Br | H | |
| 8 | $CH_3$ | H | |

TABLE 10

Compounds of formula Ia wherein $R_2$-A denotes a group of formula XI':

![Structure XIa] (XIa)

| No. | $R_{11}$ | $R_{12}$ | Mp. [°C.] |
|---|---|---|---|
| 1 | $NH_2$ | H | |
| 2 | $CONH_2$ | H | |
| 3 | Cl | H | |
| 4 | Cl | Cl | |
| 5 | H | H | |
| 6 | H | $CH_3$ | |
| 7 | $CH_3$ | H | |
| 8 | $CH_3$ | $CH_3$ | |

TABLE 11

Compounds of formula Ia wherein $R_2$-A denotes a group of formula XII or XIII':

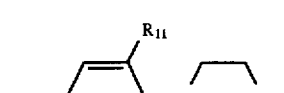

(XIIa)

wherein $R_{14}$ and $R_{15}$ represent the groups $R_3$ and $R_4$, respectively, but together additionally represent
—$CH_2$—$CJH_2$—$CH_2$—$CH_2$—

| No. | $R_{14}$ | $R_{15}$ | Form | Mp. [°C.] |
|---|---|---|---|---|
| 1 | H | $CH_3$ | | |
| 2 | $CH_3$ | H | | |
| 3 | $CH_3$ | $CH_3$ | cis | |
| 4 | $CH_3$ | $CH_3$ | trans | |
| 5 | $C_2H_5$ | $CH_3$ | cis/trans | |
| 6 | $C_2H_5$ | $C_2H_5$ | cis | |
| 7 | $C_2H_5$ | $C_2H_5$ | trans | |
| 8 | H | H | | 240-3 |
| 9 | H | i-$C_3H_7$ | | |
| 10 | —$CH_2$—$CH_2$—$CH_2$—$CH_2$— | | cis | |
| 11 | —$CH_2$—$CH_2$—$CH_2$—$CH_2$— | | trans | |

TABLE 12

Compounds of formula Ia wherein $R_2$-A denotes a group of formula XIV', the positional data for $R_5$ and $R_6$ relating to the quinazolinone ring system

| No. | $R_7$ | $R_5$ | $R_6$ | Mp. [°C.] |
|---|---|---|---|---|
| 1 | H | H | H | |
| 2 | H | 6-$OCH_3$ | 7-$OCH_3$ | |
| 3 | H | 8-$OCH_3$ | H | |
| 4 | H | 6-OH | 7-OH | |
| 5 | H | 7-OH | H | |
| 6 | H | 8-OH | H | |
| 7 | H | 6-Cl | H | |
| 8 | H | 6-$CH_3$ | 7-$CH_3$ | |
| 9 | $CH_3$ | H | H | |
| 10 | $CH_3$ | 6-$OCH_3$ | 7-$OCH_3$ | |
| 11 | $CH_3$ | 8-$OCH_3$ | H | |
| 12 | $CH_3$ | 6-OH | 7-OH | |
| 13 | $CH_3$ | 7-OH | H | |
| 14 | $CH_3$ | 8-OH | H | |
| 15 | $CH_3$ | 6-Cl | H | |
| 16 | $CH_3$ | 6-$CH_3$ | 7-$CH_3$ | |

TABLE 13

Compounds of formula Ia wherein $R_2$-A denotes a group of formula XV'

| No. | m | $R_3$ | Mp. [°C.] |
|---|---|---|---|
| 1 | 2 | H | |
| 2 | 2 | $CH_3$ | |
| 3 | 2 | $C_2H_5$ | |
| 4 | 2 | n-$C_3H_7$ | |
| 5 | 2 | n-$C_4H_9$ | |
| 6 | 2 | i-$C_3H_7$ | |
| 7 | 3 | H | |
| 8 | 3 | $CH_3$ | |
| 9 | 3 | $C_2H_5$ | |
| 10 | 3 | n-$C_3H_7$ | |
| 11 | 3 | n-$C_4H_9$ | |
| 12 | 3 | i-$C_3H_7$ | |

TABLE 14

Compounds of formula Ia with various groups of formula $R_2$, and A denoting 1,4-piperazindiyl

| No. | $R_2$ | Mp. [°C.] |
|---|---|---|
| 1 | phenyl | 270–3 |
| 2 | 2-pyrimidinyl | 200–3 |
| 3 | 2-pyrazinyl | 245–8 |

What is claimed is:

1. A compound of formula I

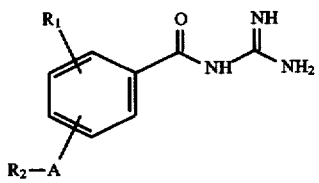

wherein $R_1$ is R'—$SO_2$— or R'—NH—$SO_2$— (R' being $C_1$–$C_5$-alkyl, halogen or phenyl-substituted $C_1$–$C_5$-alkyl, in which the phenyl groups may contain up to three substituents selected from the group consisting of halogen, $C_1$–$C_4$-alkyl or $C_1$–$C_4$-alkoxy), F, Cl or $CF_3$;

$R_2$—A— is a group of formula

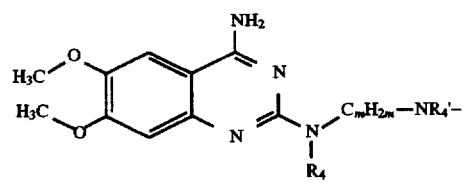 (II')

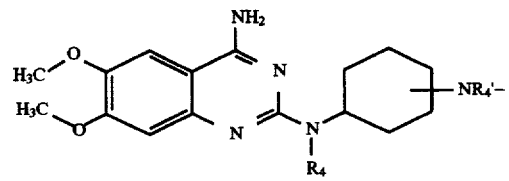 (III')

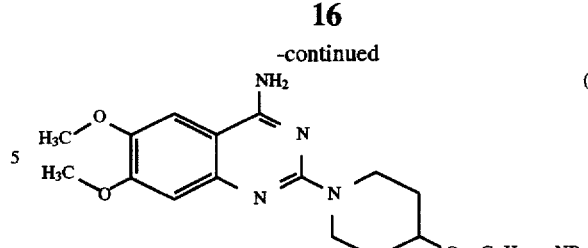 (IV')

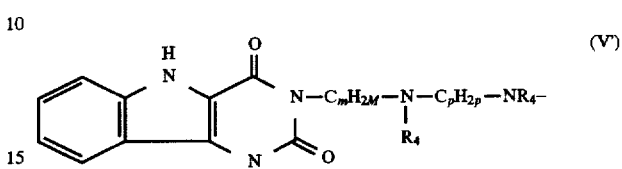 (V')

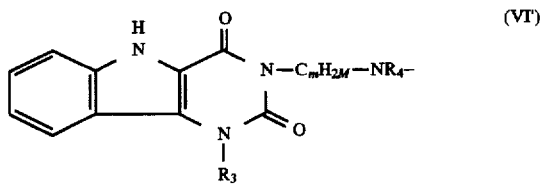 (VI')

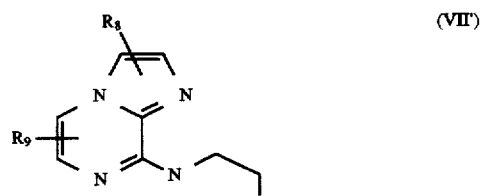 (VII')

 (VIII')

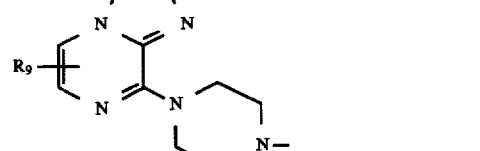 (VIII')

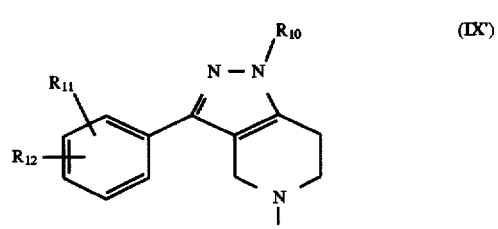 (IX')

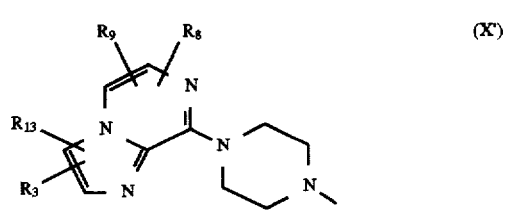 (X')

17

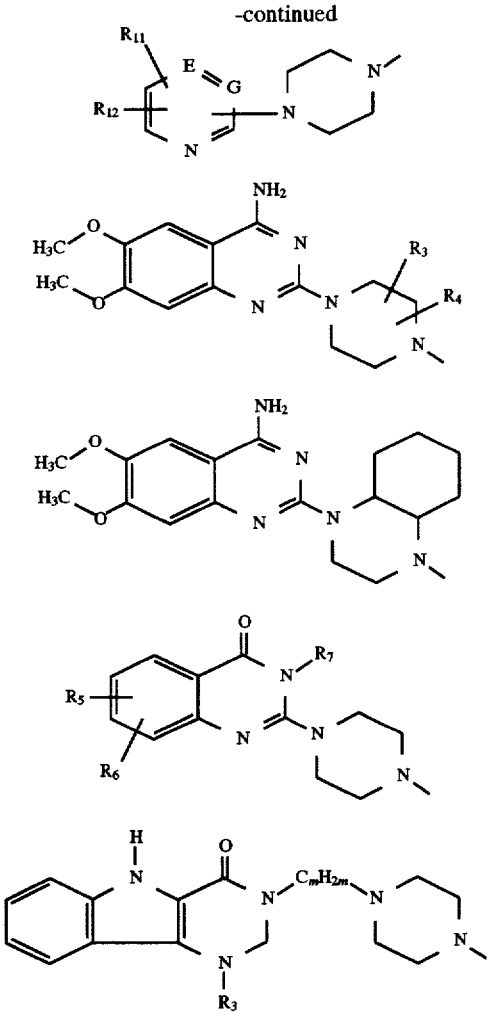

wherein

R$_3$, R$_4$ and R$_4$' which may be the same or different, are hydrogen or a C$_1$–C$_3$-alklyl radical and R$_4$ and R$_4$' may also be phenyl, benzyl or C$_3$–C$_7$-cycloalkyl;

R$_5$ and R$_6$, which may be the same or different, are hydrogen, methyl, methoxy, hydroxy or halogen;

R$_7$ is hydrogen, C$_1$–C$_4$-alkyl, benzyl or benzyloxy;

R$_8$ and R$_9$, which may be the same or different, are hydrogen, C$_1$–C$_4$-alkyl, phenyl or halogen;

R$_{10}$ is hydrogen or C$_1$–C$_6$-alkyl, which may also be substituted by phenyl or methyl-, methoxy- or halogen-substitute phenyl;

R$_{11}$ and R$_{12}$, which may be the same or different, are hydrogen, methyl, methoxy, phenyl, benzyl, nitro, cyano, halogen, trifluormethyl, amino, NR$_{10}$R$_{13}$, 1-pyrrolidinyl, 1-pyrazolinyl, 1-imidazolidinyl, 1-piperidinyl, 1-piperazinyl or carbamoyl, R$_{11}$ may also be a benzene ring fused by condensation, which may have up to three substituents selected from the group consisting of methyl, methoxy, halogen, CF$_3$ and CN;

18

R$_{13}$ is hydrogen, C$_1$–C$_4$-alkyl, which may also be substituted by phenyl, phenoxy, benzyloxy or halogen;

E and G, which may be the same or different, are N or CH, or

R$_2$ is phenyl optionally substituted up to three times with R$_{11}$ and or R$_{12}$, which may be the same or different, and A is a structure selected from the group consisting of the following

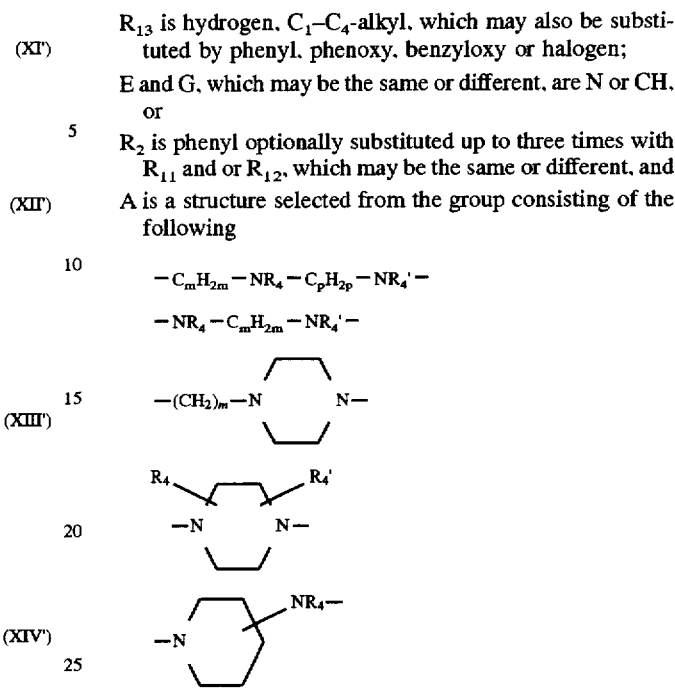

and m is an integer selected from the group consisting of 2,3,4,5 and 6, n is 0 or 1 and p is 2,3 or 4, an individual stereoisomer, or cis/trans-isomer or a mixture of such isomers thereof.

2. The compound as recited in claim 1, where R$_2$—A— is

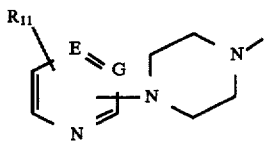

and E or G is N.

3. The compound as recited in claim 1,

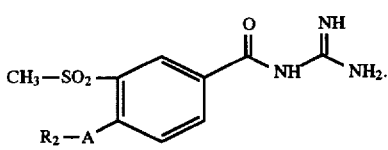

4. A pharmaceutical composition of matter comprising a compound as recited in claim 1 and a pharmaceutically acceptable carrier or excipient.

* * * * *